United States Patent
Dupont et al.

(10) Patent No.: US 9,694,182 B2
(45) Date of Patent: Jul. 4, 2017

(54) DEVICES FOR ELECTRICAL STIMULATION OF A BIOLOGICAL TISSUE AND METHOD FOR CALIBRATING SAME

(71) Applicant: COMMISSARIAT A L'ENERGIE ATOMIQUE ET AUX ENE ALT, Paris (FR)

(72) Inventors: Florent Dupont, Chatillon (FR); Jean-Francois Beche, Villeurbanne (FR); Cyril Condemine, Izeaux (FR); Pascale Pham, Crolles (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 75 days.

(21) Appl. No.: 13/888,780

(22) Filed: May 7, 2013

(65) Prior Publication Data
US 2013/0317563 A1 Nov. 28, 2013

(30) Foreign Application Priority Data
May 7, 2012 (FR) ...................................... 12 54166

(51) Int. Cl.
*A61N 1/36* (2006.01)
(52) U.S. Cl.
CPC ..... *A61N 1/36132* (2013.01); *A61N 1/36128* (2013.01)
(58) Field of Classification Search
CPC .......................... A61N 1/36128; A61N 1/36132
USPC ......................................... 607/45, 48, 62, 54
See application file for complete search history.

(56) References Cited

U.S. PATENT DOCUMENTS 6,128,537 A * 10/2000 Rise ................................ 607/45
7,974,696 B1 7/2011 DiLorenzo

FOREIGN PATENT DOCUMENTS

WO WO 2006/044793 A2 4/2006

OTHER PUBLICATIONS

French Preliminary Search Report issued Sep. 7, 2012, in French Application No. 12 54166 filed May 7, 2012.
C. Ionescu, et al., "Activating Paralyzed Muscles using Adaptive Control and a Neuroprosthetic Technique", 2006 IEEE International Conference on Automation, Quality and Testing, Robotics, May 1, 2006, 5 pages.
Han-Chang Wu, et al., "A Versatile Multichannel Direct-Synthesized Electrical Stimulator for FES Applications", IEEE Transactions on Instrumentation and Measurement, vol. 51, No. 1, Feb. 1, 2002, 8 pages.

* cited by examiner

*Primary Examiner* — Alyssa M Alter
(74) *Attorney, Agent, or Firm* — Oblon, McClelland, Maier & Neustadt, L.L.P.

(57) ABSTRACT

An electrical stimulation system including: a mechanism generating at least one electrical signal to be applied to a biological tissue that is to stimulated and measuring a response of the biological tissue to each electrical signal; a calculation mechanism estimating, based on each electrical signal and on a corresponding response of the biological tissue, at least one parameter of an electrical model of the biological tissue and its interface with the electrical stimulation system and determining, using the model, at least one parameter of a stimulation pulse to be applied to the biological tissue by the electrical stimulation system; and a mechanism generating a stimulation pulse to be applied to the biological tissue.

10 Claims, 5 Drawing Sheets

DEVICES FOR ELECTRICAL STIMULATION OF A BIOLOGICAL TISSUE AND METHOD FOR CALIBRATING SAME

The invention relates to the technical field of the electrical stimulation of biological tissues, notably neurostimulation. To that end, the invention proposes an electrical stimulator comprising means allowing self-calibration thereof and an integrated circuit for controlling such a stimulator; the invention also proposes a method for calibrating an electrical stimulation system.

The invention applies in particular, although not exclusively, to implantable electrical stimulators, notably for deep brain stimulation, retinal stimulation, cochlear stimulation, stimulation of the vagus nerve, etc.

Conventional electrical stimulators deliver pulses of current or of voltage the waveform of which is predetermined.

Figure 1:
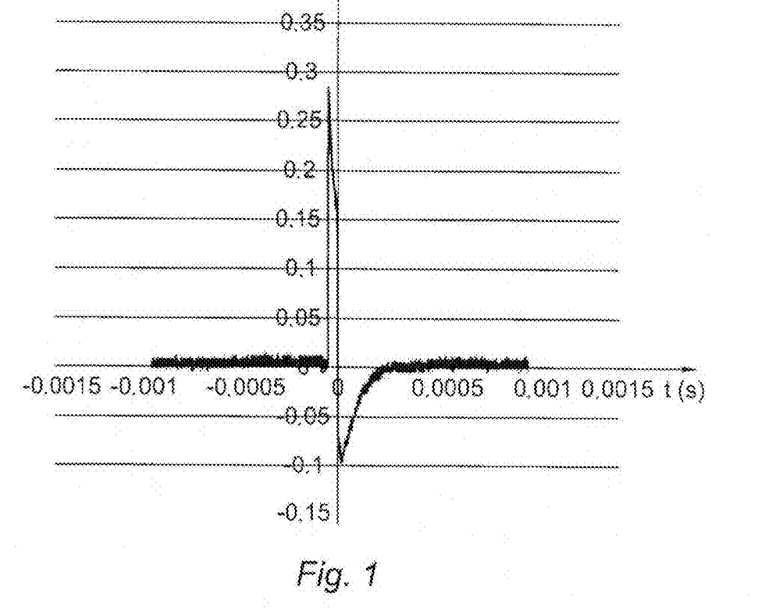
FIG. 1: an electrical pulse of the "Lilly" type.

The brain stimulators used in clinical practice mainly employ what are known as "Lilly" pulses (see FIG. 1), introduced by Dr John C Lilly in his publication "Injury and Excitation by Electric Currents—A. The Balanced Pulse-Pair Waveform", chapter 6 of the book entitled "Electrical Stimulation of the Brain", published by Daniel E. Sheer, editor, University of Texas Press for Hogg Foundation for Mental Heath, Austin, Tex., on pages 60-64, 1961.

In chronic brain stimulation (long-term implantation) the problem that arises is that of remaining above the stimulation threshold without causing tissue damage. Lilly pulses have proven themselves to be particularly well-suited to achieving this objective. While the choice of the waveform of the signal is fixed, the surgeon has to adapt the amplitude and pulse repetition frequency thereof in order to obtain the desired clinical signs. For example, for a deep brain stimulator, the usual stimulation parameters for treating Parkinson's disease are: –3V for the peak amplitude and 130 Hz for the pulse repetition frequency of the Lilly pulses.

For retinal stimulation, although this technique is still not very developed and far less refined than the deep brain stimulation techniques, the signals most commonly used are two-phase squarewave pulses comprising a positive phase followed by a negative one, or vice versa. The voltage values are generally between 90 mV and 10.5 V, and the values for current are generally between 7 nA-25 mA; the durations generally range between 1 µs and 10 ms.

One disadvantage with the prior art is that the pulse actually received by the tissue that is to be stimulated does not exactly correspond to the pulse delivered by the stimulator. In the case of voltage pulses, what happens is that the biological tissue and interface with the stimulator (and more specifically its electrodes) behave like a filter, deforming the pulse. Furthermore, the parameters of these filters can change over time, depending on the biological and chemical environment in which the electrodes are situated. For example, one of the causes of this or these modifications is the growth of fibrous tissue or gliosis around the electrode and corrosion of the materials of which the implant is made. This has a number of undesirable consequences: the therapeutic efficacy of the stimulation may be compromised (in some cases the modified pulses may even cause lesions), and the power consumption of the stimulator may be needlessly high. In the case of current pulses, an increase in the impedance perceived by the electrodes may lead to the output stages of the stimulator becoming saturated.

The invention seeks to alleviate the abovementioned disadvantages of the prior art.

One first subject of the invention is an electrical stimulation system comprising: a means for generating at least one electrical signal to be applied to a biological tissue that is to be stimulated and for measuring a response of said biological tissue to said or each said electrical signal; a calculation means for estimating, based on the knowledge of said or of each said electrical signal and on the corresponding response of said biological tissue, at least one parameter of an electrical model of said biological tissue and its interface with said electrical stimulation system and for determining, using said model, at least one parameter of a stimulation pulse to be applied to said biological tissue by means of said electrical stimulation system, and a means for generating a said stimulation pulse to be applied to said biological tissue.

This electrical stimulation system may be of implantable type, and notably chosen from: an implantable deep brain stimulation apparatus; an implantable retinal stimulation apparatus; an implantable apparatus for stimulating the vagus nerve; an implantable cortical stimulation apparatus and an implantable muscle stimulation apparatus.

According to one particularly advantageous embodiment, said calculation means may be designed (which means designed specifically, configured and/or programmed) to estimate a transfer function of said electrical model and to determine at least one parameter of said stimulation pulse to be applied to the biological tissue on the basis of said transfer function.

More particularly, according to one preferred embodiment, said calculation means may be designed to determine at least one parameter of said stimulation pulse to be applied to the biological tissue on the basis of said transfer function and of a predetermined reference pulse.

According to another preferred embodiment, the calculation means may be designed to determine said stimulation pulse parameter in such a way that at least one parameter of the pulse actually applied to the biological tissue adopts a value equal to a reference value, with a predefined margin of error. This reference value may notably correspond to a corresponding parameter (for example a peak voltage) of a predefined reference pulse.

Another subject of the invention is an integrated circuit for controlling an electrical stimulation system, comprising: a means for generating at least one electrical signal to be applied to a biological tissue that is to stimulated and for measuring the response of said biological tissue to said or each said electrical signal; a calculation means for estimating, based on the knowledge of said or of each said electrical signal and on the corresponding response of said biological tissue, at least one parameter of an electrical model of said biological tissue and its interface with said electrical stimulation system and for determining, using said model, at least one parameter of a stimulation pulse to be applied to said biological tissue by means of said electrical stimulation system.

According to one particularly advantageous embodiment, said calculation means may be designed (which means specifically designed, configured and/or programmed) to estimate a transfer function of said electrical model and to determine at least one parameter of said stimulation pulse to be applied to the biological tissue on the basis of said transfer function.

More particularly, according to one preferred embodiment, said calculation means may be designed to determine at least one parameter of said stimulation pulse to be applied to the biological tissue on the basis of said transfer function and of a predetermined reference pulse.

According to another preferred embodiment, the calculation means may be designed to determine said stimulation pulse parameter in such a way that at least one parameter of the pulse actually applied to the biological tissue adopts a value equal to a reference value, with a predefined margin of error. This reference value may notably correspond to a corresponding parameter (for example a peak voltage) of a predefined reference pulse.

Such an integrated circuit may also comprise a means for generating a said stimulation pulse to be applied to said biological tissue.

Yet another subject of the invention is a method for calibrating a system for the electrical stimulation of a biological tissue, comprising the steps involving:
a. using said electrical stimulation system for applying at least one electrical signal to said biological tissue and for measuring the response of said biological tissue to said or to each said electrical signal;
b. from knowledge of said or of each said electrical signal and of the corresponding response of said biological tissue, automatically estimating at least one parameter of an electrical model of said biological tissue and of its interface with said electrical stimulation system; and
c. using said electrical model to determine automatically at least one parameter of a stimulation pulse to be applied to said biological tissue using said electrical stimulation system.

According to various embodiments:
such a method may involve the use of stimulation electrodes of said electrical stimulation system in order to implement said step a
step c may involve the use of said electrical model to estimate a transfer function of the biological tissue and of its interface with said electrical stimulation system, and the determination of at least one parameter of said stimulation pulse to be applied to said biological tissue on the basis of said transfer function.
step c may involve determining said parameter of the stimulation pulse in such a way that at least one parameter of the pulse actually applied to the biological tissue adopts a value equal to a reference value, with a predefined margin of error.
said steps b and c may be implemented by calculation means of said electrical stimulation system.

Other features, details and advantages of the invention will become apparent from reading the description given with reference to the attached drawings provided by way of example and which respectively depict.

Figure 2:
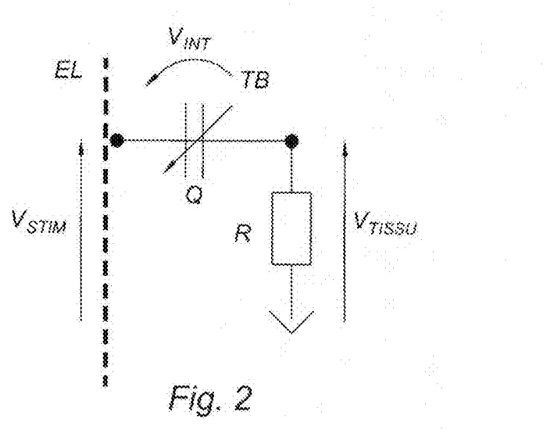
FIG. 2: an equivalent electrical circuit modeling a biological tissue and its interface with a stimulation electrode.

Numerical modeling and in vivo impedance measurements demonstrate that the system made up of a biological tissue and of its interface with an electrode behaves like a filter that can be modeled as an equivalent electrical circuit comprising reactive and resistive elements. The simplest model is a series RQ circuit forming a high-pass filter as illustrated in FIG. 2. The R element models the electrical resistance of the tissue; the Q element is a "constant-phase element" that models the imperfect dielectric behavior of the interface. A constant-phase element is a passive element the (complex) impedance $Z_{CPE}$ of which has a phase angle that is independent of the frequency, equal to $-(90 \times n)°$:

$$Z_{CPE} = \frac{1}{Q_0(i\omega)^n}$$
$$= \frac{1}{Q_0 \omega^n} e^{-\frac{\pi}{2}ni}$$

where $\omega$ is the angular frequency of the signal, $Q_0 = |Z_{CPE}|^{-1}$ at $\omega=1$ rad/s and $0 \leq n \leq 1$. In FIG. 2, $V_{STIM}$ is the stimulation voltage applied by the electrical stimulator (assuming the use of a voltage signal, which is the most common scenario) through the electrode EL and $V_{TISSU}$ is the voltage actually applied to the tissue TB; $V_{INT}$ is the voltage drop at the interface, such that the $V_{STIM} = V_{INT} + V_{TISSU}$.

A resistor and a capacitor may be considered to form the extreme boundaries of constant-phase elements: n=0 in the case of a resistor, which implies a zero phase angle; n=1 in the case of a capacitor, which implies a phase angle of −90°. When the constant-phase element is an ordinary capacitance, the circuit of FIG. 2 becomes a series RC filter.

Figure 3A:
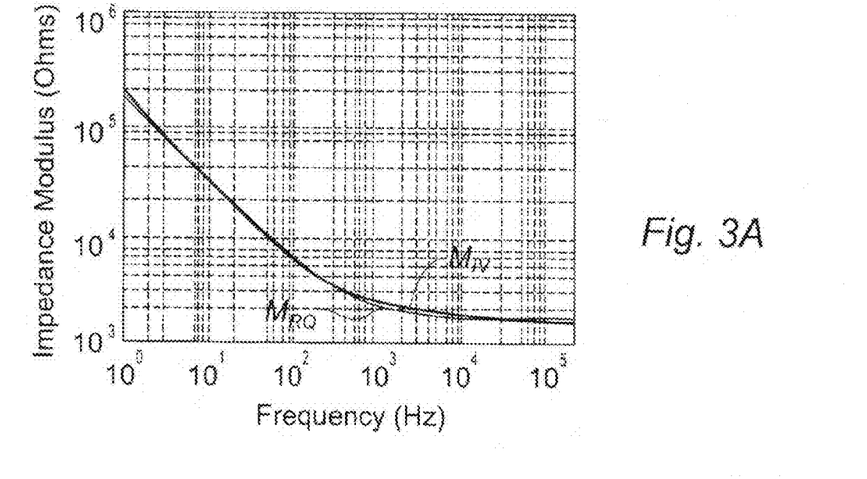
FIGS. 3A-3B: the modulus and phase of the impedance spectrum of the system formed of the brain of a monkey and its interface with a deep brain stimulation millimeter electrode, measured in vivo, and of an RC electric filter that models this interface.
Figure 3B:
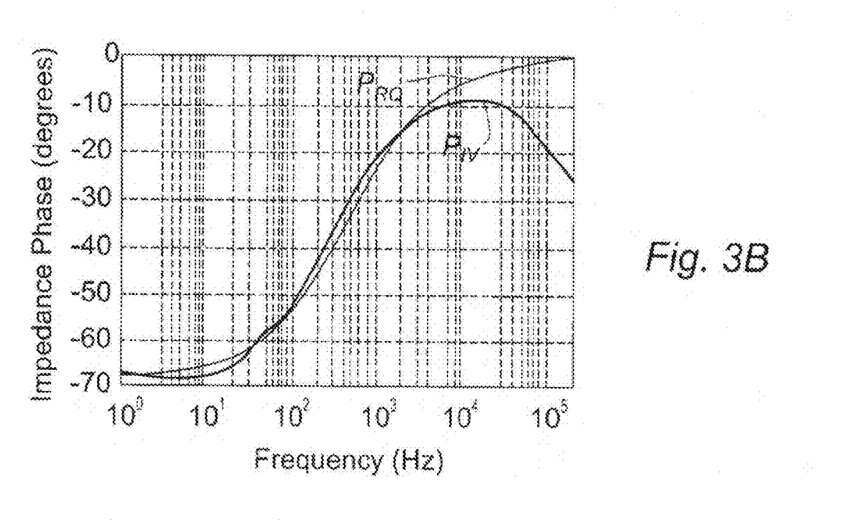
Figure 4A:
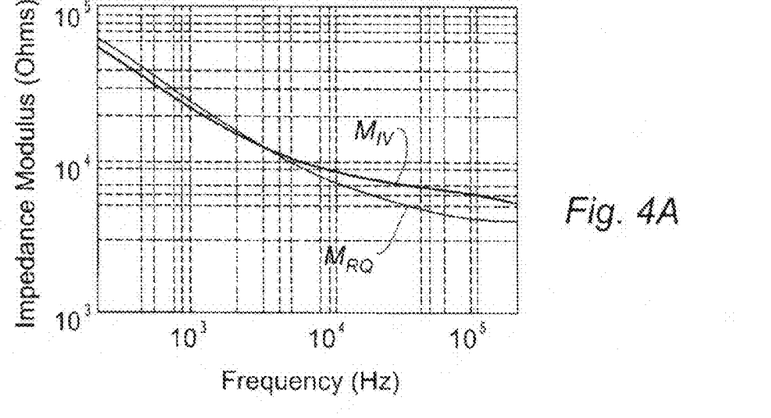
FIGS. 4A-4B: the modulus and phase of the impedance spectrum of the system consisting of the retina of a rat and its interface with an array of microelectrodes, measured in vivo, and of an electric RC filter that models this interface.
Figure 4B:
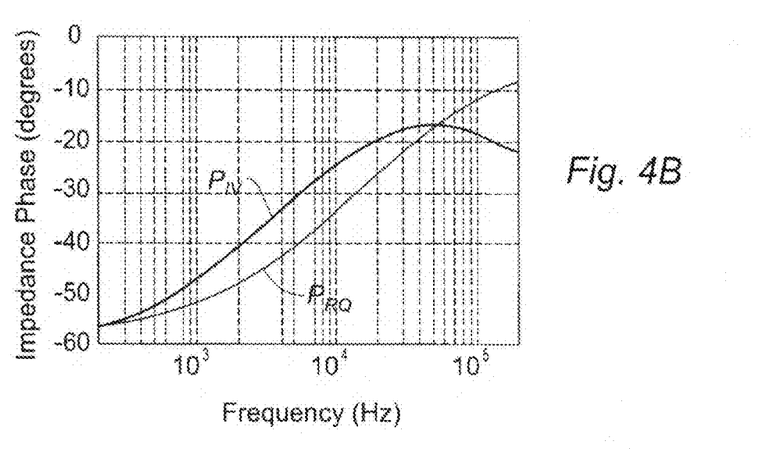

The values of R, $Q_0$ (or C if n is set equal to 1) and, where applicable, of n, can be adjusted in such a way as to reproduce as faithfully as possible—for example using a least squared error criterion over a range of frequencies of interest—the value of the complex impedance of the interface—tissue system. For example:

in FIG. 3A (or 3B) the curve $M_{IV}$ (or $P_{iv}$) represents the modulus or phase angle) of the impedance of a deep brain stimulation millimeter electrode (Electrode Medtronic, see 3389 http://professional.medtronic.com/pt/neuro/dbs-md/prod/dbs-lead-model-3389/index.htm) with the brain tissue of a monkey (macaque), measured in vivo as a function of the frequency; the curve $M_{RQ}$ (or $P_{RQ}$) represents the modulus (or the phase angle) of the input impedance of the RC filter best modeling this system. This gives the following values: R=1665 Ω, $Q_0$=429 nF.s$^n$ where n=0.76. In the case of the constant-phase element, the units of $Q_0$ are given in [F] (Farad) per $[s]^{n-1}$. Thus, the product $Q_0 \cdot \omega^n$ is expressed in $[F] \cdot [s]^{n-1} \cdot [s]^{-n}$, i.e. $[F] \cdot [s]^{-1}$ which is consistent with the product $C \cdot \omega$ in the case of a capacitance.

in FIG. 4A (or 4B) the curve $M_{IV}$ (or $P_{IV}$) represents the modulus (or the phase angle) of the impedance of an array of retinal microelectrodes which is implanted under the retina of a rat, measured in vivo as a function of the frequency; the curve $M_{RQ}$ (or $P_{RQ}$) represents the modulus (or the phase angle) of the input impedance of the RC filter best modeling this system. The following values are found: R=40870Ω, $Q_0$=13.37 nF·s$^{n-1}$, where n=0.83.

Figure 5:
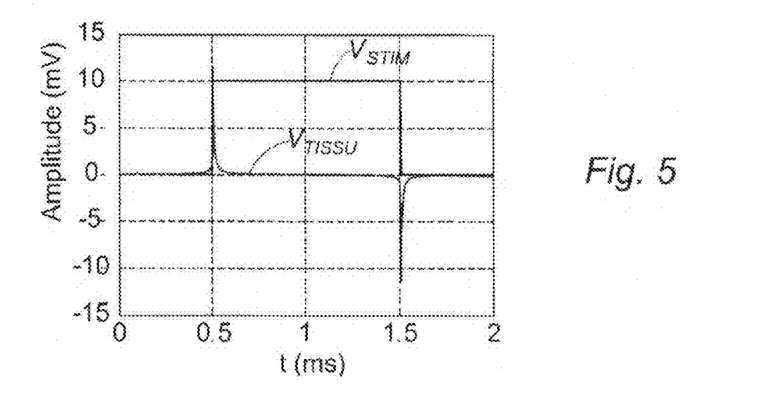
FIG. 5: the deformation of a square-wave pulse that is caused by the system made up of the biological tissue and its interface with a retinal microelectrode.

The deformation introduced by the tissue and its interface with the electrode is illustrated in FIG. 5 in the case of simulation pulse of the square wave voltage type, with an amplitude of 10 mV and a duration of 200 μs, applied between two circular micrometer electrodes having a radius of 50 μm spaced 100 μn apart (edge to edge); these are values that are typical in retinal stimulation. For this type of stimulation, use is made, for example, of an array of 9 electrodes as defined hereinabove, set out in three rows of three electrodes. The parameter's of the filter modeling this are: R=17.7kΩ, $Q_0$=3.3 nF·s$^{n-1}$, where n=0.801.

It may be clearly seen that the pulse $V_{TISSU}(t)$ actually applied to the retinal tissue differs widely from the pulse $V_{STIM}(t)$ generated by the stimulator. In particular, it is far shorter, because $V_{TISSU}(t)$=0 for t>60 μs approximately, whereas the $V_{STIM}$ remains at a "high" value for 200 μs.

Figure 6A:
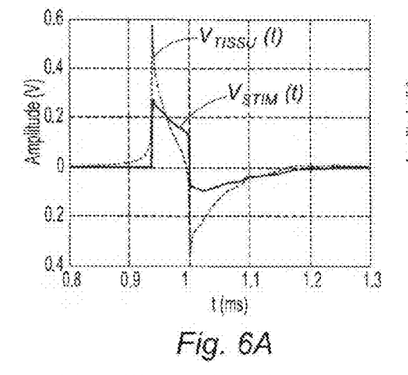
FIGS. 6A and 6B: the deformation of a "Lilly" pulse which is brought about by the system consisting of a biological tissue and its interface with a deep brain stimulation electrode and with a retinal microelectrode, respectively.
Figure 6B:
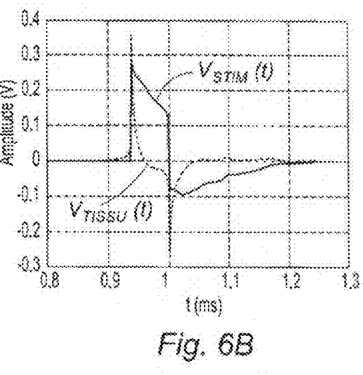

FIG. 6A shows that a "Lilly" voltage pulse is deformed by a millimeter electrode of the type commonly used in deep brain stimulation (R=17 Ω; $Q_0$=33.5 μF·s$^{n-1}$), employed on a monkey. FIG. 6B shows that the deformation is far greater in the case of a microelectrode of a retinal stimulation array, implanted in a rat, the medium then being modeled by the parameters of the electrode: R=17.7 kΩ; $Q_0$=3.35 nF·s$^{n-1}$. Thus, for the same stimulation pulse, the signal actually applied to the tissue ($V_{TISSU}(t)$) varies according to the biological medium. That can detract from the therapeutic efficacy of the stimulation.

One idea underlying the invention is to take account of the filter effect introduced by the system made up of the biological tissue and its interface with a stimulation electrode in order to calibrate an electrical stimulator.

More specifically, according to the invention, an electrical stimulator is used to characterize the system with which it interacts—tissue and interface—to determine the parameters of an electrical model of this system (self-calibration) and to use these parameters to optimize the waveform and/or the duration of the stimulation pulses. In that way it is possible to adapt the waveform of the stimulation system to suit the filter identified, so as to keep control over the waveform and amplitude of the signal actually applied to the tissue.

Figure 7:
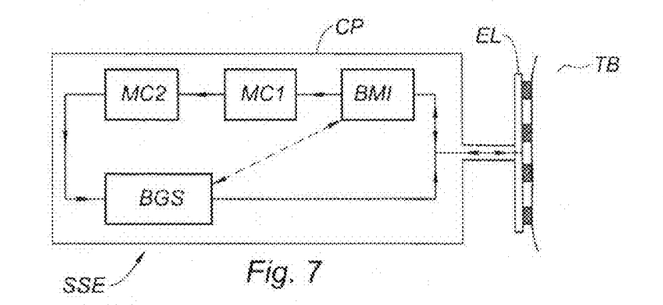
FIG. 7: the block diagram of an electrical stimulator according to one embodiment of the invention.

FIG. 7 shows a block diagram of an electrical stimulator SSE according to one embodiment of the invention. This stimulator comprises at least one stimulation electrode—or electrode array—EL, intended to come into contact with a biological tissue TB that is to be stimulated, and an electronic control circuit CP which, amongst other things, generates the stimulation pulses that will be applied to the tissue TB via the electrode or electrodes EL.

As discussed above, the electrode or array of electrodes EL may differ widely in shape/geometry and dimensions according to the intended application, ranging from a single electrode with a surface area of a few square millimeters for deep brain stimulation to an array of several tens or hundreds of planar of three-dimensional microelectrodes, having individual surface areas of the order of around ten or a hundred or so square micrometers, for retinal or cochlear stimulation. In what follows, consideration will be given to an array of circular planar electrodes each having a radius of 50 μm, with an electrode spacing (edge to edge) of 100 μm.

The biological tissue TB is in a saline medium, containing Na$^+$ and Ca$^+$ ions at a concentration of around 138 nM, together with proteins and cells; its conductivity is empirically estimated to be 1.4178 S/m.

The electronic circuit for controlling the stimulator notably comprises:
  an impedance measurement unit BMI, for generating at least one electrical signal to be applied to the tissue TB, typically by means of the electrode/array of electrodes EL, and for measuring (typically by means of this same electrode or array of electrodes) a response of said biological tissue to said or to each said electrical signal;
  a first calculation means MC1 for adjusting the parameters of an electrical model (series RQ, series or more elaborate RC) to suit the measurements taken by the unit BMI;
  a second calculation means MC2 for determining the waveform and/or the intensity and/or the duration of a stimulation pulse on the basis of the parameter values determined by the unit MC1; and
  a signal generator unit BGS for generating this stimulation pulse; the unit BGS may also collaborate with the unit BMI to generate the signals that are to be applied to the tissue TB when measuring the impedance.

These units are not necessarily physically distinct from one another. For example, the various calculation operations, or some of them, may be performed by different wired logic circuits or alternatively by a single processor that has been programmed accordingly. All, or just some, of these units may be combined into a digital or digital/analog hybrid dedicated integrated circuit ("ASIC"). Not all of the stimulation system is necessarily implanted with the electrodes. Only the effector part (the signal generator unit) may for example be implemented in an ASIC, the rest of the signal processing and control functions being removed to an external circuit (FPGA, microcontroller, etc).

The unit BMI may perform impedance spectroscopy by passing a weak sinusoidal current between two stimulation electrodes (bipolar configuration) and measuring the voltage at their terminals, this measurement being repeated for several sinusoidal-current frequency values.

As an alternative, the electrodes may be used to apply a voltage pulse to the tissue and measure its response in terms of current (or, conversely, the tissue may be stimulated using current and it response measured in terms of voltage). Next, the impedance is estimated using various signal processing techniques; in this regard reference may be made to the article by M. Min et al. "*Broadband excitation for short-time impedance spectroscopy*", Physiol. Meas. 29 (2008) S185-S192.

The impedance thus measured is used by the first calculation means MC1 to adjust the parameters of an electrical model (equivalent electrical circuit) of the system made up of the electrode/tissue interface and the tissue itself. Next, said first calculation means determines the transfer function H of this equivalent electrical circuit.

Figure 8:
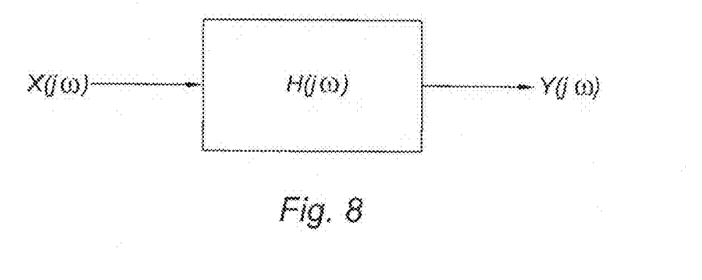
FIG. 8: how a transfer function between a signal X and a signal Y is determined.

What is meant by the transfer function is the function that links the voltage $V_{TISSU}$ (or the current) applied to the tissue to the stimulation voltage $V_{STIM}$ (or current). More specifically, referring to FIG. 8, if X represents the input signal of the transfer function (the stimulation voltage or current $V_{STIM}$) and Y represents the output signal of the transfer function (voltage or current applied to the tissue $V_{TISSU}$), then:

$$H(j\omega) = \frac{Y(j\omega)'}{X(j\omega)}$$

-continued $$= \frac{V_{TISSU}(j\omega)}{V_{STIM}(j\omega)}$$

X(jω) and Y(jω) respectively denoting the Laplace transforms of the time-based expressions of X and Y, X(t) and Y(t) respectively, such that:

$$X(t)=L^{-1}[X(j\omega)]$$

$$Y(t)=L^{-1}[Y(j\omega)]$$

Where L denotes the Laplace transform operator.

It is also possible to use a measurement configuration referred to as monopolar, with just one stimulation electrode and a passive return "at infinity", which means to say an electrode of large size (surface area at least ten times higher than that of the stimulation electrode), referred to as the "counter electrode", situated at a distance that by far exceeds the radius of action of the stimulation electrode. Thus, this "counter electrode" has no influence on the form of the electric field generated by the working electrode.

Thus, in general, the calculation means MC1 makes it possible to estimate a transfer function H linking the electrical signal generated by the stimulator (for example $V_{STIM}$) and the electrical signal actually applied to the medium (for example the tissue).

Using this transfer function H, the second calculation means MC2 determines a waveform (for example an amplitude and/or duration) of the stimulation pulse. This can be done on the basis of a number of algorithms, examples of which are given hereinbelow.

Figure 9A:
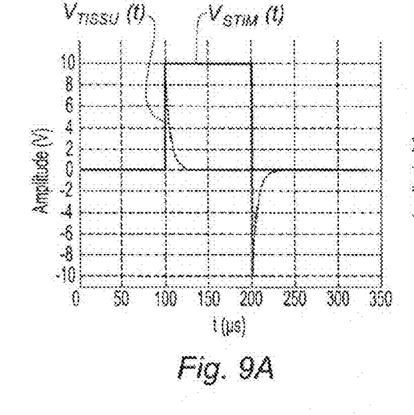
FIGS. 9A and 9B: a first algorithm for determining the duration and/or waveform of a stimulation pulse.
Figure 9B:
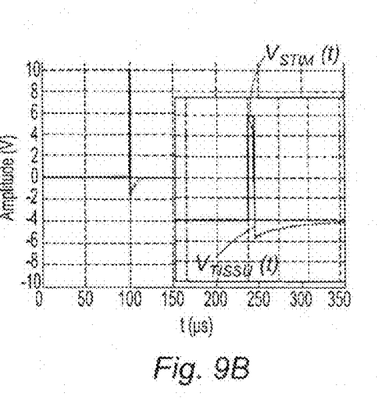

One first algorithm, illustrated by FIGS. 9A and 9B, stimulates this same equivalent circuit and increasingly reduces the width of the pulse $V_{STIM}$. This pulse then increasingly resembles the original signal—whatever the waveforms thereof (square in the example considered here). The algorithm stops when the waveform of the stimulated signal $V_{TISSU}(t)$ is deemed by the operator to be sufficiently close to $V_{STIM}(t)$ Sufficiently close means that a parameter of the signal $V_{TISSU}(t)$, for example the maximum amplitude and/or the minimum amplitude, corresponds to that of the signal $V_{STIM}(t)$, to within a percentage that has been predetermined by the operator. FIG. 9A relates to the case of a squarewave pulse of "long" duration, for which $V_{TISSU}(t)$ differs greatly from the $V_{STIM}(t)$, while FIG. 9B illustrates the case of a far shorter squarewave pulse, for which it can be considered that $V_{TISSU}(t) \approx V_{STIM}(t)$.

Thus the units BMI, MC1 and MC2 calibrate—or rather self-calibrate—the stimulator. This calibration is not performed once and for all but has to be repeated on a regular basis, because the properties of the tissue and of the interface are changeable.

The unit BGS is a conventional one. It receives at input the parameter or parameters defined by the unit MC2, and generates the corresponding stimulation pulses. This unit can also be used to generate the pulses used for characterizing the biological tissue; but entails direct collaboration with the unit BMI, which collaboration is indicated schematically in FIG. 2 by a double-headed arrow drawn in dotted line.

A second algorithm estimates the inverse transfer function $H_{INV}$ of the transfer function H of the medium. Thus, if a predetermined signal Y' ($V'_{TISSU}$), referred to as the reference signal, is to be applied to the medium, the algorithm makes it possible to establish the signal X ($V_{STIM}$) to be applied, such that $X(j\omega)=H_{inv}(j\omega) \cdot Y(j\omega)$. The signal actually applied to the tissue is then:

$$Y(j\omega)=H(j\omega)X(j\omega)=H(j\omega)H_{INV}(j\omega)Y'(j\omega)\approx Y'(j\omega)$$

Thus, with knowledge of the signal $V'_{TISSU}(t)$ (setpoint or reference signal) that is to be applied to the tissue, such a signal being determined a priori by the user, and with knowledge of the transfer function of the medium H, this function being determined as indicated hereinabove, the inverse function $H_{INV}$ is determined and the stimulation signal $V_{STIM}$ is determined, making it possible to generate a signal $V_{TISSU}=V'_{TISSU}$ However, estimating $H_{inv}$ may prove to be tricky because of the non-linearity of the electrical response of the medium and because of the various types of noise affecting the signals the noise being of biological and/or electronic origin. In general, the stimulation signal X is determined with knowledge of the reference signal Y', using the estimate of the transfer function H. This determination may for example be performed using an iterative control loop the objective of which is to generate a control signal X (allowing a signal to be applied to the tissue that approximates to the reference signal Y', knowing the transfer function H. After a certain time has elapsed, which corresponds to the time taken to establish a steady state, the corrector delivers a signal X such that the signal Y applied to the tissue (or one of the parameters thereof) corresponds to the reference signal Y' (or one of the parameters thereof), give or take an error.

Figure 10:
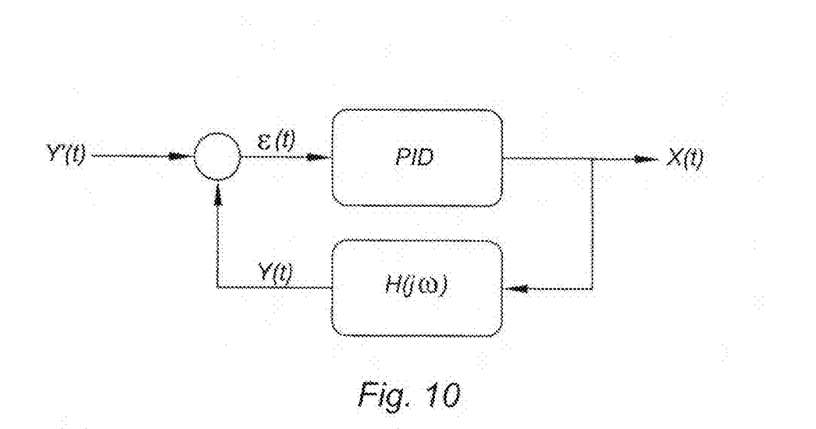
FIG. 10 a second algorithm for determining the duration and/or waveform of a stimulation pulse.

Such a feedback loop may use a PID (Proportional, Integral, Derivative) controller, as depicted in FIG. 10.

The invention applies to instances in which the stimulation pulses are controlled in terms of voltage, because it is in that mode of operation that the deformations introduced by the tissue/interface system are the greatest. It also applies to the cases of controlled current pulses, the stimulus applied to the tissue being identical to that generated by the stimulator. However, the voltage generated is proportional to the impedance of the tissue and/or is liable to lead to saturation of the output stages of the stimulator. Now, if this impedance is very high (of the order of several MΩ at low frequency), a weak current may generate a very high voltage, which is harmful to the tissues. Under these conditions, the ability of the stimulator to characterize the tissue means that the maximum permissible current can be determined, and lesions caused by excessively high voltage values can be avoided.

The invention claimed is:

1. An electrical stimulator comprising at least:
   one stimulation electrode, or electrode array, configured to come into contact with a biological tissue that is to be stimulated;
   an electronic control circuit which generates the stimulation pulses to be applied to the tissue via the electrode or electrodes;
   a means for generating at least one calibration electrical signal to be applied to a biological tissue that is to be stimulated and for measuring a response of said biological tissue to said or each said calibration electrical signal;
   a calculation means for
      estimating, based on the knowledge of said at least one calibration electrical signal and on the corresponding response of said biological tissue, at least one electrical parameter of an electrical model of a system made up of said biological tissue and its interface with said electrode or electrodes, the said system being modeled as an equivalent electrical circuit comprising reactive and resistive elements, and for determining, using said model, at least one stimulation pulse parameter of a stimulation pulse to be applied to said biological tissue by means of said electrical stimulator, the said stimulation pulse being different from the said calibration electrical signal, and the said at least one electrical parameter of an electrical model and the said at least one stimulation pulse parameter of a stimulation pulse being distinct, wherein said calculation means estimates a transfer function of said electrical model and determines the at least one stimulation pulse parameter of said stimulation pulse to be applied to the biological tissue on the basis of said transfer function and of a predetermined reference pulse, the said transfer function being a function that links the voltage or the current applied to the biological tissue to the stimulation voltage or current, and a means for generating a said stimulation pulse to be applied to said biological tissue.

2. The electrical stimulator as claimed in claim 1, in which said calculation means is designed to determine said stimulation pulse parameter in such a way that at least one parameter of the pulse adapted to be applied to the biological tissue adopts a value equal to a reference value, with a predefined margin of error.

3. The electrical stimulator as claimed in claim 1, configured to be implantable and selected from the group consisting of:
   an implantable deep brain stimulation apparatus
   an implantable retinal stimulation apparatus;
   an implantable apparatus for stimulating the vagus nerve;
   an implantable cortical stimulation apparatus; and
   an implantable muscle stimulation apparatus.

4. An integrated circuit for controlling an electrical stimulator, comprising:
   an electronic control circuit which generates the stimulation pulses adapted to be applied to the tissue via the electrode or electrodes;
   a means for generating at least one calibration electrical signal adapted to be applied to a biological tissue that is to be stimulated and for measuring the response of said biological tissue to said or each said calibration electrical signal;
   a calculation means for estimating, based on the knowledge of said at least one calibration electrical signal and on the corresponding response of said biological tissue, at least one electrical parameter of an electrical model of a system made up of said biological tissue and its interface with an electrode or electrodes, the said system being modeled as an equivalent electrical circuit comprising reactive and resistive elements, and for determining, using said model, at least one stimulation pulse parameter of a stimulation pulse adapted to be applied to said biological tissue by means of said electrical stimulator, the said stimulation pulse being different from the said calibration electrical signal, and the said at least one electrical parameter of an electrical model and the said at least one stimulation parameter of a stimulation pulse being distinct, said calculation means estimates a transfer function of said electrical model and determines the at least one stimulation pulse parameter of said stimulation pulse adapted to be applied to the biological tissue on the basis of said transfer function and of a predetermined reference pulse, the transfer function being a function that links the voltage or the current applied to the biological tissue to the stimulation voltage or current.

5. The integrated circuit as claimed in claim 4, in which said calculation means is designed to determine said stimulation pulse parameter in such a way that at least one parameter of the pulse adapted to be applied to the biological tissue adopts a value equal to a reference value, with a predefined margin of error.

6. The integrated circuit as claimed in claim 4, also comprising a means for generating a said stimulation pulse adapted to be applied to said biological tissue.

7. A method for calibrating an electrical stimulator of a biological tissue, comprising:
   a) using said electrical stimulator for applying at least one calibration electrical signal to said biological tissue and for measuring the response of said biological tissue to said or to each said calibration electrical signal;
   b) from knowledge of said at least one calibration electrical signal and of the corresponding response of said biological tissue, automatically estimating at least one electrical parameter of an electrical model of a system made up of said biological tissue and of an electrode or electrodes of said electrical stimulator, the said system being modeled as an equivalent electrical circuit comprising reactive and resistive elements; and
   c) using said electrical model to determine automatically at least one stimulation pulse parameter of a stimulation pulse adapted to be applied to said biological tissue using said electrical stimulator, the said stimulation pulse being different from the said calibration electrical signal, and the said at least one electrical parameter of an electrical model and the said at least one stimulation pulse parameter of a stimulation pulse being distinct,
   wherein the method further includes use of said electrical model to estimate a transfer function of the biological tissue and of its interface with the electrode or electrodes of said electrical stimulator, and determining and using at least one parameter of said stimulation pulse adapted to be applied to said biological tissue on the basis of said transfer function, the said transfer function being a function that links the voltage or the current applied to the biological tissue to the stimulation voltage or current.

8. The method as claimed in claim 7, in which c) includes determining said parameter of the stimulation pulse in such a way that at least one parameter of the pulse adapted to be applied to the biological tissue adopts a value equal to a reference value, with a predefined margin of error.

9. The method as claimed in claim 7, in which b) and c) are implemented by calculation means of said electrical stimulator.

10. An electrical stimulator comprising at least:
   one stimulation electrode, or electrode array, intended to come into contact with a biological tissue that is to be stimulated;
   an electronic control circuit which generates the stimulation pulses adapted to be applied to the tissue via the electrode or electrodes;
   wherein said electronic control circuit generates at least one calibration electrical signal adapted to be applied to a biological tissue that is to be stimulated and for measuring a response of said biological tissue to said or each said calibration electrical signal; estimates, based on the knowledge of said at least one calibration electrical signal and on the corresponding response of said biological tissue, at least one electrical parameter of an electrical model of a system made up of said biological tissue and its interface with said electrode or electrodes, the said system being modeled as an equivalent electrical circuit comprising reactive and resistive elements, and for determining, using said model, at least one stimulation pulse parameter of a stimulation pulse adapted to be applied to said biological tissue by means of said electrical stimulator, the said stimulation pulse being different from the said calibration electrical signal, and the said at least one electrical parameter of an electrical model and the said at least one stimulation pulse parameter of a stimulation pulse being distinct, and generates a said stimulation pulse to be applied to said biological tissue, and wherein the electronic control circuit estimates a transfer function of said electrical model and determines the at least one parameter of said stimulation pulse adapted to be applied to the biological tissue on the basis of said transfer function and of a predetermined reference pulse, the said transfer function being a function that links the voltage or the current applied to the biological tissue to the stimulation voltage or current.

* * * * *